United States Patent [19]

Perleberg

[11] Plant 4,587

[45] Aug. 12, 1980

[54] APPLE TREE (ACE STRAIN)

[76] Inventor: Carl R. Perleberg, P.O. Box 838, Quincy, Wash. 98848

[21] Appl. No.: 952,641

[22] Filed: Oct. 19, 1978

[51] Int. Cl.[2] ..... A04L 5/00

[52] U.S. Cl. ..... Plt./35

[58] Field of Search ..... Plt./35

*Primary Examiner*—Robert E. Bagwill
*Assistant Examiner*—James R. Feyrer

[57] ABSTRACT

The subject apple variety comprises a new Red Delicious sport mutation (Ace strain) originating as a limb sport on a spur variety Red Delicious apple tree. The new variety is also of the spur type. It is unique in the following characteristics: Its leaves are significantly larger than the leaves of the parent tree and other spur Red Delicious apple tree varieties; its fruit possesses superior color characteristics and a very high degree of color consistency; its fruit is significantly larger than the fruit of the Bisbee strain Red Delicious apple tree; and the flesh and under layer of the epidermis of its fruit lose their green chlorophyll coloration in high degree at an early date. Accordingly, the fruit is characterized by an unusually white flesh color.

5 Drawing Figures

DESCRIPTION

The present invention relates to a new variety of apple tree.

The accompanying drawings comprise color photographs of the branches of my new variety of apple tree and of its fruit:

Figure 1:
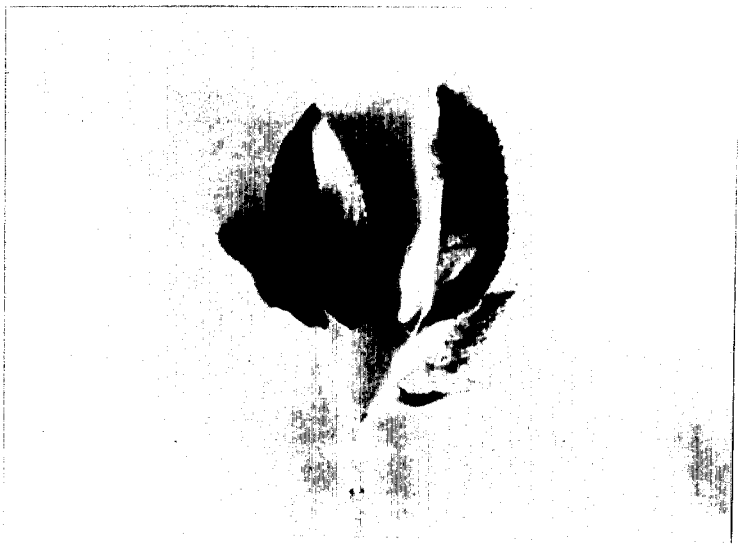
FIG. 1 is a photograph of a spur from a four-year old wood of Bisbee strain Red Delicious apple tree. The relatively small size of the leaf, typical of older spurs of spur-type delicious strains is to be noted.
Figure 2:
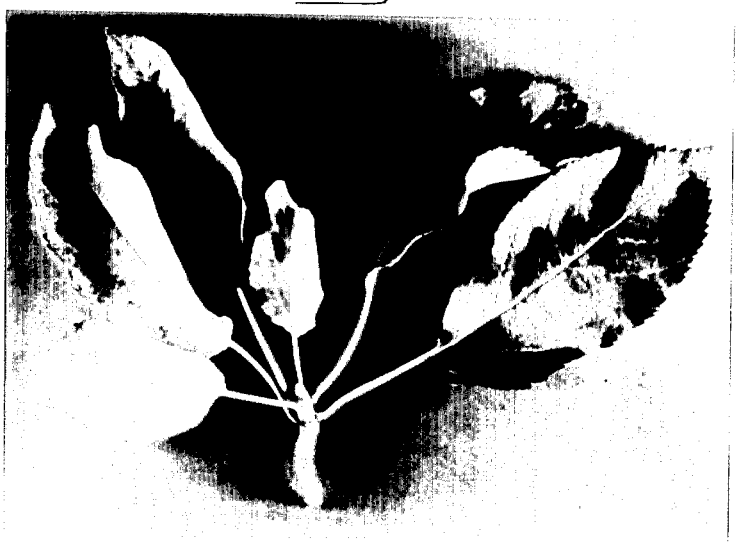
FIG. 2 is a photograph of a spur from the four-year old wood of the hereindescribed new strain (Ace strain) Red Delicious apple tree. The relatively larger leaf size of the leaves as compared with those of the Bisbee strain shown in FIG. 1 is to be noted.

The focal distances for the photographs of FIG. 1 and FIG. 2 were the same. The relative sizes of the leaves therefore are directly comparable.

Figure 3:
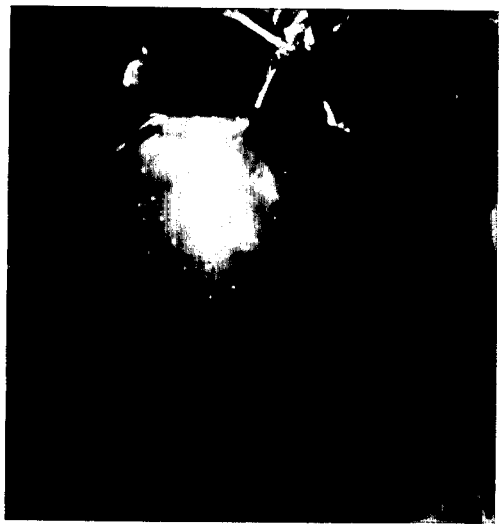
Figure 4:
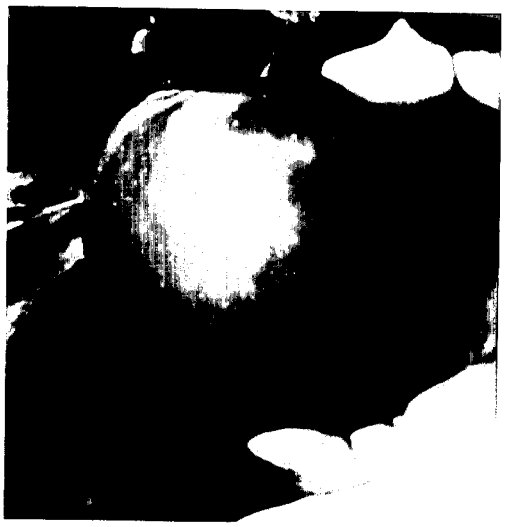

FIGS. 3 and 4 are color photographs, front and back views showing the highly developed color characteristics of the front and back of the fruit.

Figure 5:
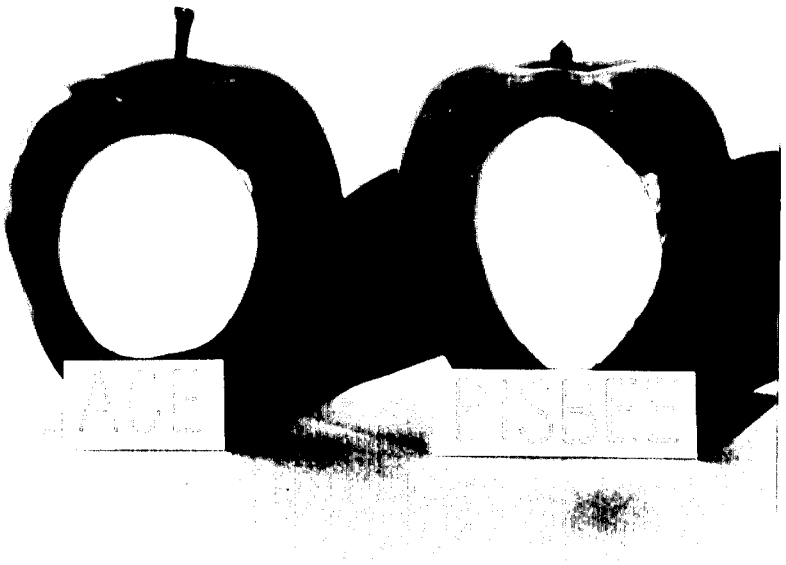

FIG. 5 is a color photograph of fruit picked on a relatively early date, i.e. Sept. 1, 1978, and showing the color of the flesh of the cut fruit of my new Ace strain of Red Delicious apple (on the left) and of the Bisbee Red Delicious apple (on the right). The absence of chlorophyll, the accompanying absence of green color, the resulting pure white flesh coloration, and the corresponding early maturity of the fruit of my new variety of apple tree are clearly evident from the photograph.

Although the fruit of my new Ace strain is significantly larger on the average than the fruit of the Bisbee, for the purposes of FIG. 5 an Ace apple has been purposely selected which is exactly the same size as the Bisbee to which the flesh color is to be compared. The flesh color is related to size, and the size is related to maturity. In other words, the Ace and Bisbee apples shown in FIG. 5 are of substantially the same maturity. At this stage of its development, the flesh of the Bisbee is distinctly green, while that of the Ace is not.

In the comparative views of FIGS. 1 and 2 and FIG. 5, the fruits of my new strain and of the control Bisbee strain were picked on the same day from trees grown on the same ranch, in the same climate, under the same soil conditions, and from the same root stock for the purpose of obtaining a valid comparison.

The presently described new and distinct variety of apple was discovered by me as a sport mutation growing on a spur-type Bisbee or Oregon Red Red Delicious apple tree in my cultivated apple orchard in Quincy, Washington. It has been reproduced to the fifth generation by budding and grafting in the aforementioned orchard and has produced fruit up through the fourth generation. It has proven to be a new and distinct mutation of a Red Delicious variety.

The second, third and fourth generation trees have been grown for purposes of comparison close to or alongside trees of the "Starkrimson" (Bisbee strain) and "Red King" Oregon Spur Delicious (Trumbull strain), commonly known as "Oregon Red". My new variety has tree growth characteristics resembling those of the above mentioned spur-type Red Delicious apple trees with the exception that the leaves are significantly larger in the center of the tree, the fruit at maturity is significantly larger than the fruit of the Bisbee strain, the external color characteristics of the fruit are distinctively different, and the fruit flesh color is unusually white.

As shown in FIGS. 1 and 2, in a typical specimen the interior spur leaves are from 30 to 100% larger than are the comparable leaves of the Bisbee Red Delicious apple tree. This is a desirable characteristic since the leaf size is an indication of sunlight-catching ability, tree health and individual spur health. The larger leaf enables the individual spur to grow a larger, high quality, well-colored fruit over a longer period of years.

Measurements of typical leaf sizes made on the largest three leaves per spur (of seven or eight leaves) on the three or four year old outside wood and six or eight year old inside wood of Ace, Oregon Red, and Bisbee apple trees are given in Table I below. The leaf size is subject to variation under different growing conditions. The tabulated sizes are for leaves picked in July, 1979 from trees of medium vigor bearing a heavy apple crop, and grown in vigorous, irrigated loam soil in intense sunlight.

TABLE I

| | ACE | | | OREGON RED | | | BISBEE | | |
|---|---|---|---|---|---|---|---|---|---|
| | Outside | Inside | Diff. | Outside | Inside | Diff. | Outside | Inside | Diff. |
| Length | 4.62 | 4.60 | .02 | 4.91 | 4.94 | .03 | 4.04 | 3.93 | .09 |
| Width | 2.11 | 2.09 | .02 | 2.28 | 2.25 | .03 | 2.10 | 1.98 | .12 |
| *Leaf area in Sq. In. | 7.019 | 6.922 | .097 | 8.060 | 8.003 | .057 | 6.108 | 5.602 | .506 |

*length × width × .72

TABLE II

| APPLES/BOX | ACE (%) | BISBEE-OREGON RED (%) |
|---|---|---|
| 72 | — | 5.4 |
| 80 | 13.7 | 5.0 |
| 88 | 24.7 | 23.5 |
| 100 | 23.3 | 23.6 |
| 113 | 13.7 | 19.2 |
| 125 | 12.3 | 8.0 |
| 138 | 5.0 | 7.0 |
| 150 | 1.4 | 4.0 |
| 163 | 5.0 | 11.0 |
| Extra Fancy | 96% | 65.5% |

My new Red Delicious sport variety is further distinguished by the unique external color characteristics of its fruit.

The red color of its fruit develops very early in a striped pattern on a green background. The starting date of fruit coloration is substantially earlier than the date of development of color in the case of the Bisbee and Oregon Red.

As is shown in FIGS. 3 and 4, the red color of the fruit develops sufficiently over the entire surface area to enable picking and marketing only about 114 days from bloom, as compared with a normal development and ripening period of about 132 days from bloom in the case of the related species referred to hereinabove.

As also shown in FIGS. 3 and 4, the color on the front side (sunnyside) and the back side (shadyside) of the fruit is well developed and substantially uniform. Also, the apples picked are consistent in high color factor. In a typical sampling of fruit picked in the year 1978 only three out of six thousand apples picked at a given time were too light to be marketed.

The outside color of my new apple variety is further characterized by being deep red, but bright, and striped. The striped pattern of the fruit persists at maturity. The red color in the areas between the stripes is of a lighter shade of red than is the darker red color of the stripes.

As shown in FIG. 5, my new apple sport variety is still further distinguishable in that the flesh and under layer of the epidermis of its fruit lose almost all signs of chlorophyll at an early date. This early loss of chlorophyll is evidenced by the absence of green coloration and by the whiteness of the flesh color, a characteristic materially enhancing the marketability of the fruit.

As compared with the conventional Bisbee and Oregon Red Apple varieties, my newly developed Ace apple variety shows improved size and other packout qualities. This is evidenced by a comparison of a commercial packout of the apples of these species at the conclusion of the 1978 crop year.

The apples were all grown on my Quincy, Washington commercial apple orchard under identical conditions, i.e. the same cover crop, the same fertilizer, the same pruning crew, the same irrigation, and the same soil during the 1978 growing season.

In the case of the Ace apples, there was no hand thinning during the growing season. In the case of the Bisbee-Oregon Red mixture, the apples were hand thinned and spaced out during the growing season.

The Ace packout comprised 100% Ace apples; the comparative packout, a mixture of 90% Bisbee and 10% Oregon Red apples. Both crops were graded by personnel of Washington Fruit Growers of Wenatchee, Wash. according to the usual standards of color, contour, freedom from blemishes, etc.

The results are as given in Table II below.

It is significant to note that the total crop of ace apples ran 96% extra fancy even without hand thinning. The Bisbee-Oregon Red mixture ran 65.5% extra fancy with hand thinning and fruit spacing. 65.5% Extra fancy is about average for the industry.

A further botanical description of my new apple variety follows:

Location where grown or observed: Quincy, Wash.

Parentage: Sport of Red King Oregon Spur Red Delicious ("Oregon Red") Plant Pat. No. 2816 or Star Crimson Delicious (Bisbee Strain) Plant Pat. No. 1565.

Dates of first and last picking: 124 (Sept. 3) to 158 (Oct. 7) days from bloom dates.

Tree: Medium; moderately vigorous, twice as tall as wide; dense; hardy; regular bearer; very productive.

Trunk: Medium stockiness; medium smoothness through the first 8 years.

Branches: Medium thickness; smooth; many spurs on limbs; Lenticels medium small.

Leaves: Medium large; medium wide; long length; thick; ovate; taper-pointed.

*Length.*—About $4\frac{5}{8}''$.

*Width.*—About $2\frac{1}{8}''$.

*Color.*—Dark green Pantone R 349. Leaf size similar throughout tree.

Flowers: Medium early.

*Dates of first full bloom.*—About Apr. 29 and May 2 respectively.

*Color.*—White with tinge of carmine.

Fruit:

*Maturity when described.*—Eating ripe about Oct. 15.

*Size.*—Uniformly large for moderately dense fruit. Axial diameter — from about 3 to $3\frac{3}{8}''$. Transverse diameter — 3 -1/16 to $3\frac{1}{2}''$.

*Form.*—Conical.

*Cavity.*—Symmetrical; flaring toward apex; depth — about $\frac{1}{2}''$. Breadth — about $1\frac{1}{4}''$, pubescent toward apex.

*Stem.*—Uniform medium stout; pubescent. Length about 1 inch. Breadth — about 3/32 inch.

*Calyx.*—Closed; both outer and inner surface pubescent.

*Skin.*—Medium thickness; tough; smooth; glossy; waxed; color Pantone R202; striped.

*Lenticels.*—Obscure; many small, depressed, circular; color of lenticels — white.

*Flesh.*—Color — satin white; juicy; firm; fine; crisp. Flavor — sweet.

*Core.*—Medium length, about $\frac{5}{8}''$; breadth about $\frac{3}{8}''$.

Seeds: From 5 to 9 and usually all perfect; no more than 2 per cell.

*Color.*—Pantone R181.

*Storage quality.*—Excellent — about 180 days in ordinary cold storage.

Having thus described my new and distinct variety of apple tree, I claim:

1. The new and distinct spur variety of Red Delicious apple tree characterized particularly, as contrasted with other spur varieties of Red Delicious apple trees, by the relatively large size of its interior spur leaves indicative of superior vigor and ability to support large, high quality fruit over long periods of time; by the early development of the red color of its fruit; by the uniformity of the red color on the front and back sides of its fruit; by the large size and deep red but bright color of its fruit; by the high color factor consistency of its fruit; and by the loss of chlorophyll in the flesh and underlayer of the epidermis of its fruit at an early date, substantially as shown and described.

* * * * *